(12) United States Patent
Blum

(10) Patent No.: US 7,582,783 B2
(45) Date of Patent: Sep. 1, 2009

(54) ANALGESICS, ANAESTHETICS, ANTIFOULANTS, AVERSANTS, IRRITANTS, INCAPACITANTS AND COMPOSITIONS CONTAINING THE SAME

(75) Inventor: Mel Blum, Wantagh, NY (US)

(73) Assignee: White Flower Associates LLP, Farmingdale, NY (US)

( * ) Notice: Subject to any disclaimer, the term of this patent is extended or adjusted under 35 U.S.C. 154(b) by 516 days.

(21) Appl. No.: 11/387,277

(22) Filed: Mar. 23, 2006

(65) Prior Publication Data

US 2007/0225515 A1    Sep. 27, 2007

(51) Int. Cl.
C07C 233/05    (2006.01)
A61K 31/20     (2006.01)

(52) U.S. Cl. .......................... 554/52; 554/51; 514/559; 106/18; 106/21

(58) Field of Classification Search .................... 554/51, 554/52; 514/559; 106/18.21
See application file for complete search history.

(56) References Cited

U.S. PATENT DOCUMENTS

| 4,652,577 | A | 3/1987 | Hollander et al. |
| 5,397,385 | A | 3/1995 | Watts |
| 5,629,045 | A | 5/1997 | Veech |
| 5,674,496 | A | 10/1997 | Etscorn et al. |
| 5,698,191 | A | 12/1997 | Wiersma et al. |
| 5,891,919 | A | 4/1999 | Blum et al. |
| 5,985,010 | A | 11/1999 | Etscorn et al. |
| 6,207,290 | B1 | 3/2001 | Blum et al. |
| 6,465,022 | B1 | 10/2002 | Torres |

Primary Examiner—Shailendra Kumar
(74) Attorney, Agent, or Firm—Jordan and Hamburg LLP

(57) ABSTRACT

Compounds and compositions the same. Method of making the compounds. The compounds and/or compositions used as an analgesic, anaesthetic, antifoulant, aversant, irritant, sternutator, neurodegenerator, counter irritant (delayed), rubifaciant, stomachic, fungicide, insecticide, preservative, circulatory stimulant, cardio-protective agent, immune booster, decongestant, anti-inflammatory agent, incapacitant, biocide, mildewcide, pharmaceutical, repellent, flavorant, carminative, antismoking agent, and/or antithrombotic agent. One of the compounds being lidocaine nonivamide. The compositions comprising one or more of: the compounds, one or more of an antioxidant, a UV absorber, and one or more biocides such as, for example, OBPA.

33 Claims, No Drawings

ANALGESICS, ANAESTHETICS, ANTIFOULANTS, AVERSANTS, IRRITANTS, INCAPACITANTS AND COMPOSITIONS CONTAINING THE SAME

BACKGROUND OF THE INVENTION

1. Field of the Invention

The present invention pertains to various compounds, methods of producing the compounds, compositions containing the compounds, and methods of using the compounds and the compositions containing the compounds. Some examples are to use the compounds as pharmaceuticals, aversive agents and/or as antifoulants. One of the compounds is lidocaine nonivamide. This compound, as well as many of the other compounds, are utilized as antifouling agents either alone or in a composition, especially a composition comprising 10,10'-oxybisphenoxarsine (OBPA) or other organo-arsenicals or biocidal antifoulants and molluscicides.

2. Description of Related Art

U.S. Pat. No. 6,207,290 to Blum et al. discloses antifoulant compositions including 10,10'-oxybisphenoxarsine and/or phenarsazine oxide with a quaternary ammonium salt. In particular, U.S. Pat. No. 6,207,290 discloses denatonium capsaicinate as one of the quaternary ammonium compounds.

U.S. Pat. No. 4,652,577 to Hollander et al. and U.S. Pat. No. 4,661,504 to Hollander et al. disclose denatonium saccharide to protect an article against gnawing, biting, licking, and feeding by various animals.

U.S. Pat. No. 5,891,919 to Blum et al. discloses denatonium capsaicinate and its use as an aversive agent, biocide, antifoulant, and flavorant. Denatonium capsaicinate is formed by reaction of a denatonium compound with capsaicin. Although the patent discloses that the combination of lidocaine or a lidocaine derivative in an aqueous, glycol, polyol, dimethylsulfoxide (DMSO), alcohol solution or combination thereof with capsaicin or any of its derivatives will form some denatonium capsaicinate, this is incorrect. In order to form a denatonium compound from lidocaine, a benzyl group, such as benzyl chloride, must first be reacted with the lidocaine. Additionally, U.S. Pat. No. 5,891,919 fails to distinguish between synthetic capsaicin and nonivamide. Although nonivamide is sometimes referred to as a synthetic capsaicin or a homologue of capsaicin, it is not capsaicin since its molecular structure and chemical and physical properties are quite different. U.S. Pat. No. 5,891,919 refers to nonivamide as synthetic capsaicin even though this is not correct since nonivamide is a capsaicinoid. There are many different capsaicinoids and capsaicinates.

U.S. Pat. No. 6,465,022 to Torres discloses a method for providing an extract of capsicum, which contains a capsaicinoid and terpene.

U.S. Pat. No. 5,985,010 to Etscorn et al. and U.S. Pat. No. 5,674,496 to Etscorn et al. disclose extraction of natural capsaicinoids from chile peppers. Both patents also disclose using the extract to minimize damage to objects caused by animals, especially by gnawing and chewing.

U.S. Pat. No. 5,698,191 to Wiersma et al. discloses a biorepellent amount of capsicum oleoresin and an amount of a saponin sufficient to enhance the effectiveness of the capsicum oleoresin.

U.S. Pat. No. 5,629,045 to Veech discloses antifoulant coatings that include capsaicin and nonivamide. Veech states that capsaicin can be extracted from cayenne pepper.

U.S. Pat. No. 5,397,385 to Watts discloses an anti-fouling coating that uses capsaicin as an antifouling agent. The patent also discloses utilizing synthetic capsainoid compounds such as synthetic capsaicin (C) and synthetic dihydrocapsaicin (DHC).

BRIEF SUMMARY OF THE INVENTION

The invention recognizes novel compounds having various characteristics, including having antifouling, analgesic, anaesthetic, mildewcidal, biocidal, pharmaceutical, aversant, repellent, flavorant, carminative, and antismoking agent properties. The invention includes the compounds themselves, the methods for their production, compositions comprising the compounds, and uses of the compounds and of the compositions. One important aspect of the invention involves the compound lidocaine nonivamide, which has many useful characteristics, including antifouling and pharmaceutical properties. Lidocaine nonivamide or a composition containing lidocaine nonivamide is very effective as an antifoulant, for example. A composition comprising lidocaine nonivamide as a co-biocide can further comprise OBPA and/or copper and/or copper oxides and/or organo-tins for excellent results as, inter alia, an antifoulant.

Another composition with excellent results is a combination of nonivamide and OBPA and/or other organo-arsenicals. Both nonivamide and OBPA are known as antifoulants. However, mixing them together improves their performance synergistically. The results are significantly better than either OBPA or nonivamide separately. A composition comprising OBPA and nonivamide can have antifoulant properties that last 25% to 100% longer than either OBPA or nonivamide separately. The scope of the invention includes a composition comprising capsaicin and OBPA as an effective antifoulant. It should be noted, however, that using nonivamide instead of capsaicin provides longer protection at a much more economical price.

The invention also encompasses other novel compounds with antifoulant, pharmaceutical and other useful properties as described below.

DETAILED DESCRIPTION OF THE INVENTION

The invention is directed to novel compounds having various uses, including having antifouling, analgesic, anaesthetic, biocidal, aversant, repellent, pharmaceutical, flavorant, carminative, irritant, incapacitant, and antismoking properties. Some of these compounds may also have useful cardiovascular benefits such as, for example, being antithrombotic. Many of these capsaicinoid compounds and homologs that have pharmaceutical, antifouling, and other properties are related in that they contain a "caine" functionality, such as lidocaine nonivamide, etc. For the purpose of brevity, a list of compounds will be referred to as the "caine compounds" and whenever "caine compounds" appears in this description, this will be a reference to the following compounds: lidocaine capsaicinate, benzocaine capsaicinate, bupivacaine capsaicinate, mepivacaine capsaicinate, cocaine capsaicinate, ambucaine capsaicinate, betoxycaine capsaicinate, butacaine capsaicinate, butoxycaine capsaicinate, dibucaine capsaicinate, etidocaine capsaicinate, fomocaine capsaicinate, hexylcaine capsaicinate, meprylcaine capsaicinate, myrtecaine capsaicinate, octacaine capsaicinate, orthocaine capsaicinate, piperocaine capsaicinate, prilocaine capsaicinate, procaine capsaicinate, propanocaine capsaicinate, propoxycaine capsaicinate, pseudococaine capsaicinate, pyrrocaine capsaicinate, risocaine capsaicinate, tetracaine capsaicinate, tolycaine capsaicinate, lidocaine nonivamide, benzocaine nonivamide, bupivacaine nonivamide, mepivacaine nonivamide, cocaine nonivamide, ambucaine nonivamide, betoxycaine nonivamide, butacaine nonivamide, butoxycaine nonivamide, dibucaine nonivamide, etidocaine nonivamide, fomocaine nonivamide, hexylcaine nonivamide, meprylcaine nonivamide, myrtecaine nonivamide, octacaine nonivamide, orthocaine nonivamide, piperocaine nonivamide, prilocaine nonivamide, procaine nonivamide, propanocaine nonivamide, propoxycaine nonivamide, pseudococaine nonivamide, pyrrocaine nonivamide, risocaine nonivamide, tetracaine nonivamide, and tolycaine nonivamide. In addition to capsaicin and nonivamide based compounds, homologs of capsaicin and nonivamide can also form the base of the compounds of the invention such as dihydrocapsaicin, nordihydrocapsaicin, homodihydrocapsaicin, homocapsaicin, n-vanillyl octanamide, n-vanillyl decanamide, n-vanillyl nonamide, n-vanillyl undecanamide, n-vanillyl paaipine acidamide, etc.

The invention includes the compounds themselves, methods for their production, compositions comprising the compounds, and uses of the compounds and compositions. One important aspect of the invention involves a composition comprising one or more of the above-mentioned compounds and further comprising OBPA. A group of compounds will be referred to as the "other biocides" and the group includes: phenarsazine oxide (PZO), copper, cupric oxides, copper sulfides, cuprous oxides, copper pyrithione, zinc pyrithione, iodo propynyl butyl carbamate, metalaxyl, niclosamide, metaldehyde, fentin acetate, copper quinolinolate, copper thiocyanate, selenium disulfide, iodine, iodine pentoxide, "organo arsenicals", thimerosal, chlor-thalinal, organo-tins, triazines, organomercurials, octyl iso-thiazolone, and/or dichloro octyl iso thiazolone. The "organo arsenicals" include, but are not limited to, arsanilic acid, roxarsone, methyl arsonic acid, mono methyl arsinic acid, mono sodium methyl arsonate (MSMA), and cacodylic acid.

One composition that is particularly effective is one comprising nonivamide and OBPA. Both OBPA and nonivamide are known antifoulants. However, mixing them together synergistically improves their performance. The results are significantly better than either OBPA or nonivamide separately. A composition comprising OBPA and nonivamide has antifouling properties that last 25% to 100% more than either OBPA or nonivamide separately. When a composition comprising OBPA and nonivamide is combined with other antifoulants such as one or more of the "other biocides" (see above for listing), the results improve by an additional 25-200%.

The invention is also directed towards a composition comprising capsaicin and OBPA, which is an effective antifouling composition. However, using nonivamide instead of capsaicin provides longer protection than capsaicin and OBPA. Nonivamide is far more economical than capsaicin and more stable and easier to synthesize.

The above-identified "caine compounds" and/or nonivamide have many uses. A composition comprising one or more of these "caine compounds" and/or nonivamide and further comprising OBPA and/or one or more of the "other biocides" is useful. Uses for the various compounds and compositions are that of local anaesthetic (topically or by injection), analgesic, desensitizing agent for diabetic neuropathy, and an antifoulant primarily for hard fouling (excellent for barnacles and zebra mussels). The compounds and compositions work exceptionally well with various co-biocides for soft fouling. The compounds and compositions also work well as irritants and sternutators in personal protection pepper sprays, neurodegenerators, counterirritants (delayed), rubifacients, carminatives, stomachics, repellents for insects, birds, fish and animals, biocides, fungicides, mildewcides, circulatory stimulants, cardio-protective agents (depressant as anti-arrhythmic and fibrin dissolver), immune boosters, decongestants, and anti-inflammatory substances. All the uses mentioned regarding this invention apply to the compounds themselves and to the compositions comprising one or more of the "caine compounds," and/or nonivamide, and/or capsaicinate, and/or OBPA and/or one or more of the "other biocides", and/or one or more antioxidants, and/or one or more UV absorbers. All the uses mentioned regarding the "caine compounds" also apply to the compounds taught by Examples 1-3 below.

The compounds and/or compositions with and without biocides disclosed above can, inter alia, be dispersed into polymers, plasticizers, and solutions for a variety of uses such as coatings for materials or the materials themselves. For polymers, one option is to add the compounds and/or compositions of the current invention directly to the melt. The compounds and compositions of the present invention may be added to paints, stains, lacquers, varnishes, glues, adhesives, gums, resins, rubbers, polymers, coating compositions, and the like. The resultant compositions may be used to coat or impregnate a layer or film on a fiber optic cable, an electric cable, a pipe, a hose, a wall, a boat hull, or other objects. The resultant compositions can be coated on polymers, wood, metals, fabrics, etc. When applied to wood it forms an excellent wood preservative. The compounds and/or compositions of the present invention can be added to plasticizers, silicones, shellacs, epoxies, oils, waxes, and the like, and impregnated into fiberglass (requires large doses to work) and into various polymers such as polyethylenes, polypropylenes, styrenes, polyesters, polyurethanes, polyolefins, acrylics, phenolics, polyvinyl chlorides (PVCs), Teflons, nylons, rubbers, silicones and the like to form fibers, a sheath layer for wrapping around a cable, wire, hose, or the like, or for coating on a substance such as a boat hull or a metal or polymer substance. The compounds can also form part of the item to be protected itself and can be incorporated into polymer objects, for example. When added, the above-mentioned compounds can be either in liquid or solid form.

The compounds and/or compositions of the present invention may be added to coatings or polymers for forming a sheath, for example, for application to electrical wires, hoses, pipes, and the like to prevent animal attack or fouling. A coating comprising at least one of the compounds of the present invention such as paint, varnish, lacquer, stain, sealant, primers, protective coatings, and extruded films, is part of the invention and these coatings may be applied to other materials such as outdoor furniture, sheds, houses, boats, etc. The compounds of the present invention can also act as aversive agents or other contact repellents to keep animals and insects (excellent moth proofing agent, for example) away and keep animals from ingesting something containing the compounds of the present invention.

The compounds and/or compositions of the present invention may be used in a coating applied to boat hulls, propellers, rudders, underwater structures, and the like as an antifoulant. Alternatively or additionally, the compounds and compositions of the current invention may be incorporated into the materials for forming such structures. This will prevent, for example, marine life such as barnacles and algae from growing on the structures. The structures will be protected against both hard and soft fouling. Some examples of hard fouling include barnacles, mussels, snails, balanidae, mollusks, etc. Some examples of soft fouling include hydroids, worms, mites, slugs, tunicates, bryozoans, amphipods, algae, weeds, slime, sea fauna & flora, etc.

The compounds and/or compositions of the current invention can also be used as a biocide and mildewcide to prevent or stop fungi, mildew and other microorganisms from growing. The affected area can be sprayed, brushed, impregnated, or coated with a composition containing the compounds of the present invention. Treating with a sticky or paste-like compound by spraying, spreading, smearing or the like can occur as well as sprinkled with a powder that contains the compounds of the invention. The compounds and compositions of the current invention can also be microencapsulated (in, for example, a polymer) to, for example, reduce toxicity.

The compounds and/or compositions of the invention can also be added to medical dressings such as sutures and bandages and can be added to salves, creams, lotions, ointments, gels, and other like medical treatments (such as micro-encapsulated time release forms) to act as analgesics and/or anaesthetics (for both humans and animals) and/or to prevent animals from removing these materials by biting, gnawing, chewing, or licking after veterinarial procedures. Lidocaine capsaicinate and nonivamide has been reported to possess external aphrodisial properties for erectile dysfunction as well as preventing premature coital ejaculation.

The compounds and/or compositions of the current invention can also be used as insect and fish repellents. They can also be added to products such as cigarettes or nail lacquer in order to deter habits such a smoking or nail biting or incorporated into a coating to deter thumb sucking. They can also be added to dangerous household chemicals as aversants. The compounds and/or compositions of the current invention can also be used as denaturants. They can also be used as food additives and as flavorants. The flavorants can have, for example, a burning, pungent, and/or bitter taste. In fact, initial tests indicate heat tasting Scoville units as high as 11,000,000-12,400,000. The compounds and/or compositions of the current invention can be utilized as fresh and sea water antifoulants such as, for example, in fresh or seawater paints. They can be utilized to treat wood. Compositions comprising one or more of the compounds of the current invention may also further comprise fungicides and/or ultraviolet absorbers and/or antioxidants to enhance efficacy. The compositions of the current invention can be used as solutions or stains to impregnate wood, for example bulkheads, piers, docks, foundations, rail ties, posts, pilings, construction timber, and the like.

There are many ultraviolet absorbers that can be included in the compositions of the current invention including but not limited to acetaminosalol, benzalphthalide, benzophenones, 3-benzylidine camphor, benzyl salicylate, bis tetramethyl piperidinyl sebacate, bornelone, bumetrizole, butyl methoxydibenzoylmethane, cinoxate, digalloyl trioleate, diisopropyl methyl cinnamate, disodium bisethylphenyl triaminotriazine stilbenedisulfonate, disodium distyrylbiphenyl disulfonate, drometrizole, ethyl diisopropylcinnamate, ethyl methoxycinnamate, ethyl PABA (para amino benzoic acid), ethyl urocanate, etocrylene, ferulic acid, glyceryl octanoate dimethoxycinnamate, glycol salicylate, homosalate, isopropylbenzyl salicylate, isopropyl dibenzoylmethane, menthyl anthranilate, menthyl salicylate, octocrylene, octrizole, octyl salicylate, oxybenzone, octyl triazone, PABA (para amino benzoic acid), phenylbenzimidazole sulfonic acid, piperidine derivatives, polyacrylamidomethyl benzylidene camphor, potassium methoxycinnamate, potassium phenylbenzimidazole sulfonate, sodium phenylbenzimidazole sulfonate, sodium urocanate, terephthalyidene dicamphor sulfonic acid, titanium dioxide, urocanic acid, VA/Crotonates/Methacryloxybenzophenone-1 copolymer. In embodiments, the ultraviolet absorber is preferably titanium dioxide, oxybenzone, benzophenones, bis tetramethyl piperidinyl sebacate, piperidine derivatives, or mixtures thereof.

Antioxidants can also be incorporated in the compositions of the current invention. The antioxidants include, but are not limited to, high purity non-polymerized ethoxyquin, ethoxyquin phosphate, citrate, maleate, propionate, formate, ascorbic acid, ascorbyl palmitate and dipalmitate, ethyl ascorbate, ascorbyl stearate and oleate, tocopherols and tocotrienols, dodecyl and octyl gallate, gallic acid and tannic acid (including salts and esters thereof), gamma oryzanol, thioctic acid and salts, monophenols, bisphenols, thiobisphenols, polyphenols, hydroquinones, phosphites, thioesters, naphthylamines, diarylamines, p-phenylenediamines, quinolines, blended amines, 0,0-di-n-octadecyl(3,5-di-t-butyl-4-hydroxybenzyl)phosphonate, 1,6-hexamethylene bis(3,5-di-t-butyl-4-hydroxyhydrocinnamate), 1,6-hexamethylene bis(3,5-di-t-butyl-4-hydroxyphenyl)propionate), thiodiethylene bis(3,5-di-t-butyl-4-hydroxy)hydrocinnamate, thiodiethylene bis(3-(3,5-di-t-butyl-4-hydroxyphenyl)propionate), octadecyl-3-(3,5-di-t-butyl-4-hydroxyphenyl)propionate), octadecyl-3,5-di-t-butyl-4-hydroxyhydrocinnamate, 3,5-di-t-butyl-4-hydroxyhydrocinnamic acid triester with 1,3,5-tris (2-hydroxyethyl)-s-triazine-2,4,6-(1H,3H,5H)trione, N-butyryl-p-aminophenol, N-(4-hydroxyphenyl)butyramide, N-pelargonoyl-p-aminophenol, N-(4-hydroxyphenyl)pelargonamide, N-lauroyl-p-aminophenol, N-(4-hydroxyphenyl) dodecanamide, 2,6-di-t-butyl-alpha-dimethylamino-p-cresol, 2,6-di-t-butyl-4-(dimethylaminomethyl)phenol, 1,3,5-tris(4-t-butyl-3-hydroxy-2,6-dimethylbenzyl)-s-triazine-2,4,6-(1H,3H,5H)trione, nickel bis(0-ethyl(3,5-di-t-butyl-4-hydroxybenzyl)phosphonate), 2,2'-oxamidobisethyl-3-(3,5-di-t-butyl-4-hydroxyphenyl)propionate, tris(2-t-butyl-4-(2-methyl-4-hydroxy-5-t-butylphenylthio)-5-methyl) phenylphosphite, bis(3,3-bis(4-hydroxy-3-t-butylphenyl) butanoic acid)glycolester, tetrakis(2,4-di-t-butylphenyl)-4,4'-biphenylylenediphosphonite, n-propyl gallate, n-propyl-3,4,5-trihydroxybenzoate, calcium bis(0-ethyl(3,5-di-t-butyl-4-hydroxybenzyl)phosphonate), 2-mercapto-4-methylbenzimidazole, 2-mercapto-5-methylbenzimidazole, zinc salt of 2-mercaptobenzimidazole, 2-mercapto-4-methylbenzimidazole, zinc salt, 2-mercapto-5-methylbenzimidazole, zinc salt, 2-mercaptotoluimidazole, zinc 2-mercaptotoluimidazole, dioctadecyl disulfide, metal aromatic sulfonates, butylated hydroxy anisole, butylated hydroxy toluene, tertiary butyl hydroquinone, ethoxyquin, nickel di-n-butyldithiocarbamate, nickel diisobutyldithiocarbamate, nickel dimethyldithiocarbamate, 3,9-bis(3-cyclohexenyl)-2,4,8,10-tetraoxaspiro(5,5)undecane, tris(5-norbornene-2-methyl)phosphite, and/or mixtures thereof.

The compounds and compositions of the current invention may be used on and/or in fiberglass, wood, stainless steel, titanium, carbon, steel, and aluminum objects and/or surfaces such as hulls, and/or underwater bronze parts.

The compounds and compositions of the current invention act as biocidal, insecticidal, and/or termiticidal agents and can protect against termites, ants, carpenter ants, carpenter bees, wasps, hornets, spiders, caterpillars, grasshoppers, flies, earwigs, scorpions, roaches, and other wood destructive insects, bacteria, fungus, mold, algae, and against marine borers. Furthermore, the biocidal compositions also work as fungicides in textiles, leathers, rubbers, etc. The compounds of the current invention can be applied with pressure or vacuum treatment, dipping, brushing, spraying, coating, alternating hot and cold thermal baths, and/or direct injection.

To synthesize lidocaine nonivamide, lidocaine or its HCl is converted to the hydroxide with KOH and/or NaOH. This hydroxide is then reacted with nonivamide. The same procedure is followed to synthesize the other "caine compounds." Thus, lidocaine, benzocaine, bupivacaine, mepivacaine, cocaine, ambucaine, betoxycaine, butacaine, butoxycaine, dibucaine, etidocaine, fomocaine, hexylcaine, meprylcaine, myrtecaine, octacaine, orthocaine, piperocaine, prilocaine, procaine, propanocaine, propoxycaine, pseudococaine, pyrrocaine, risocaine, tetracaine, tolycaine, and/or an HCl of these compounds is converted to the hydroxide with KOH and/or NaOH and reacted with capsaicin and/or nonivamide to form the "caine compounds."

The reactants necessary to synthesize the "caine compounds" are either commercially available or can be synthesized by methods known in the art by using commercially available chemicals. The procedure mentioned above regarding the synthesis of the "caine compounds" may need to be altered, in practice, to synthesize benzocaine nonivamide and/or benzocaine capsaicinate. Benzocaine does not form a long term stable HCl or hydroxide so one option is for the reaction to be direct from base ethylaminobenzoate (also known as benzocaine) with capsaicin and/or nonivamide to form benzocaine capsaicinate and/or benzocaine nonivamide, although the yields are not as good as the yields for the hydroxide compounds that are made with KOH and/or NaOH. Another option to synthesize benzocaine nonivamide and/or benzocaine capsaicinate is to synthesize the HCl of benzocaine and then, without storing this HCl of benzocaine for extended periods of time because of the stability mentioned above, to react this HCl of benzocaine with KOH and/or NaOH and then to react the resulting hydroxide of benzocaine with capsaicin and/or nonivamide. It should be noted that the reactions mentioned above with capsaicin and/or nonivamide can also be carried out with the homologs of capsaicin and nonivamide such as dihydrocapsaicin, nordihydrocapsaicin, homodihydrocapsaicin, homocapsaicin, n-vanillyl octanamide, n-vanillyl decanamide, n-vanillyl nonamide, n-vanillyl undecanamide, n-vanillyl paaipine acidamide, etc.

Many of the reactants mentioned above which are used to form the compounds of the present invention are commercially available and information on some of them is provided below. It should be noted that any mention of capsaicin includes both the naturally-occurring as well as any that is synthesized.

Lidocaine: Molecular formula $C_{14}H_{22}N_2O$; M.W. 234.33; and CAS #137-58-6.

Capsaicin (synthetic or natural): Molecular formula $C_{18}H_{27}NO_3$; M.W. 305.41; CAS#404-86-4

Nonivamide (synthetic) aka Nonyl Vanylamide or pelargonic acid vanylamide: Molecular formula $C_{17}H_{27}NO_3$; M.W. 293.40; CAS #2444-46-4 and also 2004-3-10.

Bupivacaine: Molecular formula $C_{18}H_{28}N_2O$; M.W. 288.43; CAS #2180-92-9.

Mepivacaine: Molecular formula $C_{15}H_{22}N_2O$; M.W. 246.34; CAS #96-88-8.

Benzocaine: Molecular formula $C_9H_{11}NO_2$; M.W. 165.119; CAS #94-09-7.

Cocaine: Molecular formula $C_{17}H_{21}NO_4$; M.W. 303.35; CAS #50-36-2.

As mentioned above, one aspect of the present invention is directed towards the "caine compounds," which are believed to have the structure (I) and the structure (II) as shown below. Structure (I) is a nonivamide-based structure and structure (II) is a capsaicin-based structure.

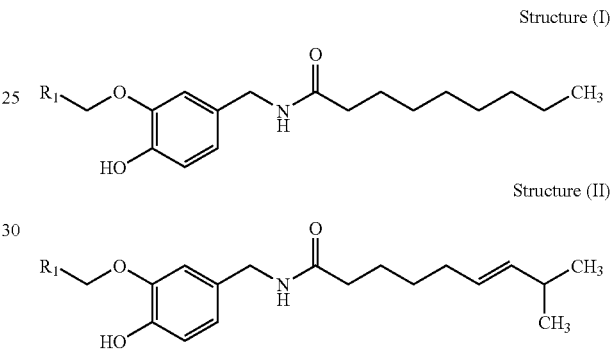

Structure (I)

Structure (II)

Where $R_1$ is a lidocaine, benzocaine, bupivacaine, mepivacaine, cocaine, ambucaine, betoxycaine, butacaine, butoxycaine, dibucaine, etidocaine, fomocaine, hexylcaine, meprylcaine, myrtecaine, octacaine, orthocaine, piperocaine, prilocaine, procaine, propanocaine, propoxycaine, pseudococaine, pyrrocaine, risocaine, tetracaine, or tolycaine functionality or residue.

Of particular importance within the "caine compounds" are lidocaine nonivamide, which is believed to have the structure (III) as shown below and lidocaine capsaicinate, which is believed to have the structure (IV) as shown below.

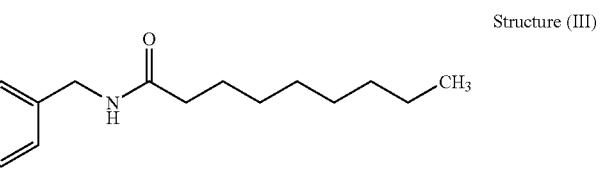

Structure (III)

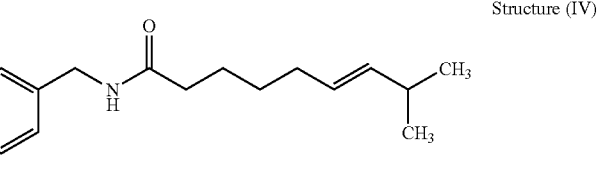

Structure (IV)

EXAMPLES

Example 1

Method of Forming Lidocaine Nonivamide and/or Lidocaine Capsaicinate

About 500 ml of pure isopropanol is added to a three necked glass flask equipped with a stirrer (60-80 rpm), thermometer, reflux (straight-run) and condenser. About 10 g of KOH (based on 100 percent content) is added to the isopropanol with stirring. The reaction mass is heated to its boiling point and held until total dissolution of the KOH occurs. The solution is then cooled to about 50-55 degrees Celsius. About 60 g of lidocaine hydrochloride is added to the cooled solution. The mixture is stirred for thirty to forty minutes at about 50-55 degrees Celsius. The resulting solution is cooled to about 18-20 degrees Celsius and transferred to a filter with filtering paper, wherein potassium chloride precipitate is separated. The mother liquor is recycled to the same flask and about 60 g (total) of nonivamide and/or capsaicin is added. The reaction mixture is heated to its boiling point and refluxed for about 1-1.5 hours. The reflux condenser is then replaced with a straight run condenser and the isopropanol-water azeotrope, if any (the water being present, for example, as an impurity in the isopropanol), is distilled off. The reaction mass is boiled off to about 200 ml in volume, cooled to an ambient temperature, and transferred to a polyethylene or similar vessel and refrigerated at about 3-5 degrees Celsius for about ten to twelve hours. The precipitated crystals are filtered, washed on a filter with cyclohexane or petroleum ether, and air or vacuum dried at ambient temperature.

Example 2

Method of Forming Benzocaine Nonivamide and/or Benzocaine Capsaicinate

About 500 ml of pure isopropanol is added to a three necked glass flask equipped with a stirrer (60-80 rpm), thermometer, reflux (straight-run) and condenser. About 60 g of benzocaine is added to the isopropanol. About 60 g of nonivamide and/or capsaicin is added. The reaction mixture is heated to its boiling point and refluxed for about 1-1.5 hours. The reflux condenser is then replaced with a straight run condenser and the isopropanol-water azeotrope, if any (the water being present, for example, as an impurity in the isopropanol), is distilled off. The reaction mass is boiled off to about 200 ml in volume, cooled to an ambient temperature, and transferred to a polyethylene or similar vessel and refrigerated at about 3-5 degrees Celsius for about ten to twelve hours. The precipitated crystals are filtered, washed on a filter with cyclohexane or petroleum ether, and air or vacuum dried at ambient temperature.

Example 3

Method of Forming the "Caine Compounds"

About 500 ml of pure isopropanol is added to a three necked glass flask equipped with a stirrer (60-80 rpm), thermometer, reflux (straight-run) and condenser. About 10 g of KOH (based on 100 percent content) is added to the isopropanol with stirring. The reaction mass is heated to its boiling point and held until total dissolution of the KOH occurs. The solution is then cooled to about 50-55 degrees Celsius. About 60 g (total) of a hydrochloride of lidocaine, benzocaine, bupivacaine, mepivacaine, cocaine, ambucaine, betoxycaine, butacaine, butoxycaine, dibucaine, etidocaine, fomocaine, hexylcaine, meprylcaine, myrtecaine, octacaine, orthocaine, piperocaine, prilocaine, procaine, propanocaine, propoxycaine, pseudococaine, pyrrocaine, risocaine, tetracaine, and/or tolycaine is added to the cooled solution. The mixture is stirred for thirty to forty minutes at about 50-55 degrees Celsius. The resulting solution is cooled to about 18-20 degrees Celsius and transferred to a filter with filtering paper, wherein potassium chloride precipitate is separated. The mother liquor is recycled to the same flask and about 60 g (total) of nonivamide and/or capsaicin is added. The reaction mixture is heated to its boiling point and refluxed for about 1-1.5 hours. The reflux condenser is then replaced with a straight run condenser and the isopropanol-water azeotrope, if any (the water being present, for example, as an impurity in the isopropanol), is distilled off. The reaction mass is boiled off to about 200 ml in volume, cooled to an ambient temperature, and transferred to a polyethylene or similar vessel and refrigerated at about 3-5 degrees Celsius for about ten to twelve hours. The precipitated crystals are filtered, washed on a filter with cyclohexane or petroleum ether, and air or vacuum dried at ambient temperature.

The present invention includes many uses for the compounds and/or compositions listed above. In addition to the uses already mentioned, the compounds and/or compositions can be incorporated into creams and/or ointments and/or solvents (such as, for example, DMSO, ethanol, alcohols, mineral oil, and/or ether) to be used in many uses as listed above including pharmaceutical uses.

The present invention envisions a composition comprising one or more of the following: nonivamide, capsaicin, one or more of the "caine compounds", one or more antioxidant, one or more UV absorber, one or more of the "other biocides", and/or OBPA. The amount of antioxidants to be used can be 0.05% to 5% by weight relative to the total weight of the composition. The amount of nonivamide, capsaicin, and/or one or more of the "caine compounds" can be 0.1% to 10% relative to the total weight of the composition. UV absorbers can be used in the amount of 0.1% to 10% by weight relative to the total weight of the composition. The biocides can be 1 to 40% of the composition depending on the biocide. The amount of nonivamide, capsaicin, one or more of the "caine compounds" or other capsaicinoids is usually (although not necessarily) one tenth of the percent of the biocide. For example, if $Cu_2O$ is used at 40%, the capsaicinoid could be 4%. If OBPA is used at 5%, the capsaicinoid could be 0.5%. All the uses mentioned regarding the "caine compounds" also apply to the compounds taught by Examples 1-3 above.

The invention claimed is:

1. A compound selected from the group consisting of: lidocaine nonivamide, benzocaine nonivamide, butacaine nonivamide, dibucaine nonivamide, procaine nonivamide, tetracaine nonivamide, lidocaine capsaicinate, benzocaine capsaicinate, butacaine capsaicinate, dibucaine capsaicinate, procaine capsaicinate, and tetracaine capsaicinate.

2. A compound of claim 1, wherein said compound is selected from the group consisting of: lidocaine nonivamide and lidocaine capsaicinate.

3. A compound of claim 1, wherein said compound is selected from the group consisting of: benzocaine nonivamide and benzocaine capsaicinate.

4. A compound of claim 1, wherein said compound is lidocaine nonivamide.

5. A composition comprising at least one of said compounds of claim 1.

6. A composition of claim 5 further comprising one or more biocides.

7. A composition of claim 6 wherein said one or more biocides comprise OBPA.

8. A composition of claim 5, further comprising one or more antioxidants.

9. A composition of claim 5, further comprising one or more UV absorbers.

10. A composition of claim 5, wherein said at least one compound comprises 0.1% to 10% of a weight of said composition.

11. A composition of claim 6, wherein said one or more biocides comprise 1-40% of a weight of said composition.

12. A composition of claim 7, wherein said OBPA comprises 1-40% of a weight of said composition.

13. A composition of claim 8, wherein said one or more antioxidants comprise 0.05 to 5% of a weight of said composition.

14. A composition of claim 9, wherein said one or more UV absorbers comprise 0.1% to 10% of a weight of said composition.

15. A composition of claim 5, further comprising a polymer.

16. A method for the production of novel compounds, comprising:
   providing hydrochlorides of one or more of the following compounds: lidocaine, benzocaine, butacaine, dibucaine, procaine, and tetracaine,
   converting said hydrochlorides of said one or more compounds to hydroxides of said one or more compounds; and
   reacting said hydroxides of said one or more compounds with capsaicin and/or nonivamide.

17. A method according to claim 16, wherein converting said hydro chlorides of said one or more compounds to hydroxides of said one or more compounds comprises reacting KOH and/or NaOH with said hydrochlorides of said one or more compounds.

18. A method according to claim 16, wherein converting said hydrochlorides of said one or more compounds to hydroxides of said one or more compounds and reacting said hydroxides of said one or more compounds with capsaicin and/or nonivamide comprises:
   adding about 500 ml of pure isopropanol to a three necked glass flask equipped with a stiffer (60-80 rpm), thermometer, reflux (straight-run) and condenser;
   adding about 10 g of KOH (based on 100 percent content) to the isopropanol with stirring;
   heating the reaction mass to its boiling point and holding it until total dissolution of the KOH occurs;
   cooling the solution to about 50-55 degrees Celsius;
   adding about 60 g (total) of a hydrochloride of lidocaine, benzocaine, bupivacaine, mepivacaine, cocaine, ambucaine, betoxycaine, butacaine, butoxycaine, dibucaine, etidocaine, fomocaine, hexylcaine, mepryl-caine, myrtecaine, octacaine, orthocaine, piperocaine, prilocaine, procaine, propanocaine, propoxycaine, pseudococaine, pyrrocaine, risocaine, tetracaine, and/or tolycaine to the cooled solution;
   stirring the mixture for thirty to forty minutes at about 50-55 degrees Celsius;
   cooling the resulting solution to about 18-20 degrees Celsius;
   transferring said resulting solution to a filter with filtering paper; and
   separating potassium chloride precipitate, the resulting liquor being a mother liquor;
   recycling the mother liquor to said three necked glass flask;
   adding about 60 g (total) of nonivamide and/or capsaicin to said three necked glass flask;
   heating a resulting mixture to a boiling point of said mixture;
   refluxing said mixture for about 1-1.5 hours;
   replacing said reflux condenser with a straight run condenser;
   distilling an isopropanol-water azeotrope, if any;
   boiling said mixture to about 200 ml in volume;
   cooling said mixture to an ambient temperature;
   transferring said mixture to a polyethylene or similar vessel;
   refrigerating said mixture at about 3-5 degrees Celsius for about ten to twelve hours;
   filtering any precipitated crystals;
   washing said crystals on a filter with cyclohexane or petroleum ether; and
   drying said crystals in air or vacuum.

19. A method for the production of novel compounds, comprising:
   reacting benzocaine with nonivamide and/or capsaicin.

20. A method according to claim 19, wherein reacting benzocaine with nonivamide and/or capsaicin comprises:
   adding about 500 ml of pure isopropanol to a three necked glass flask equipped with a stirrer (60-80 rpm), thermometer, reflux (straight-run) and condenser;
   adding about 60 g of benzocaine to the isopropanol;
   adding about 60 g of nonivamide and/or capsaicin to the isopropanol;
   heating the reaction mixture to its boiling point;
   refluxing the reaction mixture for about 1-1.5 hours;
   replacing the reflux condenser with a straight run condenser;
   distilling an isopropanol-water azeotrope, if any;
   boiling the reaction mass to about 200 ml in volume;
   cooling to an ambient temperature;
   transferring to a polyethylene or similar vessel;
   refrigerating at about 3-5 degrees Celsius for about ten to twelve hours;
   filtering the precipitated crystals;
   washing the precipitated crystals with cyclohexane and/or petroleum ether, and
   drying the precipitated crystals at ambient temperature with air or vacuum.

21. A compound made by the method of claim 16.

22. A compound made by the method of claim 17.

23. A compound made by the method of claim 18.

24. A compound made by the method of claim 19.

25. A compound made by the method of claim 20.

26. A compound made by the method of claim 16, wherein providing said hydrochlorides of said one or more compounds comprises providing hydrochlorides of one or more of the following compounds: lidocaine, benzocaine, butacaine, dibucaine, procaine, and/or tetracaine.

27. A compound made by the method of claim 16, wherein
   providing said hydro chlorides of said one or more compounds comprises providing a hydrochloride of lidocaine, and
   reacting said hydroxides of said one or more compounds with capsaicin and/or nonivamide comprises reacting said hydroxides of said one or more compounds with nonivamide.

28. A composition comprising at least one compound according to claim 1 as an analgesic, anaesthetic, antifoulant, aversant, irritant, sternutator, neurodegenerator, counter irritant (delayed), rubifaciant, stomachic, fungicide, insecticide, preservative, circulatory stimulant, cardio-protective agent, immune booster, decongestant, anti-inflammatory agent, incapacitant, biocide, mildewcide, pharmaceutical, repellent, flavorant, carminative, antismoking agent, and/or antithrombotic agent constituent of the composition.

29. A composition comprising the compound according to claim 4 as an analgesic, anaesthetic, antifoulant, aversant, irritant, sternutator, neurodegenerator, counter irritant (delayed), rubifaciant, stomachic, fungicide, insecticide, preservative, circulatory stimulant, cardio-protective agent, immune booster, decongestant, anti-inflammatory agent, incapacitant, biocide, mildewcide, pharmaceutical, repellent, flavorant, carminative, antismoking agent, and/or antithrombotic agent constituent of the composition.

30. A composition comprising at least one compound according to claim 21 as an analgesic, anaesthetic, antifoulant, aversant, irritant, sternutator, neurodegenerator, counter irritant (delayed), rubifaciant, stomachic, fungicide, insecticide, preservative, circulatory stimulant, cardio-protective agent, immune booster, decongestant, anti-inflammatory agent, incapacitant, biocide, mildewcide, pharmaceutical, repellent, flavorant, carminative, antismoking agent, and/or antithrombotic agent constituent of the composition.

31. A composition comprising nonivamide and OBPA.

32. A composition according to claim 31, wherein said nonivamide comprises 0.1% to 10% of a weight of said composition.

33. A composition according to claim 31, wherein said OBPA comprises 1-40% of a weight of said composition.

* * * * *